United States Patent [19]

Carrier

[11] Patent Number: Plant 5,293

[45] Date of Patent: Oct. 16, 1984

[54] CARNATION PLANT

[76] Inventor: Leonard E. Carrier, 1911 Sheridan Rd., Encinitas, Calif. 92024

[21] Appl. No.: 425,116

[22] Filed: Sep. 27, 1982

[51] Int. Cl. ..... A01H 5/00

[52] U.S. Cl. ..... Plt./71

[58] Field of Search ..... Plt./71, 70

*Primary Examiner*—Robert E. Bagwill

*Attorney, Agent, or Firm*—Frank B. Robb

[57] ABSTRACT

A new and distinct cultivar of carnation plant, having large, serrated flowers, strong resistance to soil borne diseases, maintains the magenta flower color, which resists fading, strong, heavy terminal with large side buds on weak secondary stems, which cultivar was originated by crossing numbered but unnamed and unpatented seedlings.

1 Drawing Figure

BACKGROUND AND DESCRIPTION OF THE INVENTION

The present invention relates to a new and distinct cultivar of Carnation plant which I designate by the name Felicia or number 2174 and which was originated by me in my commercial nursery at Encinitas, Calif. by cross-breeding numbered but unnamed and unpatented seedlings.

The primary objectives of this breeding included the production of a carnation cultivar having improved disease resistance and production qualities, along with distinctive flower color, size and form, as well as reduced tendency of the calyx to burst and cause "splits" as the flowers open fully, which is so typical of the species botanically known as *Dianthus caryophyllus*. These objectives are fully achieved, along with other desirable improvements, as evidenced by the following unique combination of principal characteristics which are outstanding in my new cultivar, Felicia and which distinguish it from its parents, as well as from all other carnations of which I am aware:

1. A very vigorous and free-breaking plant habit with strong and straight stems;
2. Superior resistance to soil-borne diseases such as *Fusarium oxysporum* and *F. roseum* and rots such as damping off, water molds, and the like.
3. Large serrated flowers which open fully without bursting the calyx and causing "splits";
4. A distinctive and attractive magenta flower color which does not fade rapidly, although ultimately fading evenly and beautifully.

Asexual reproduction of my new carnation variety by side shoot cuttings rooted in peat and "Perlite" under mist, as performed under my direction and control at Encinitas, Calif., shows that the foregoing characteristics and distinctions come true and are established and transmitted through succeeding propagations.

The accompanying drawing illustrates typical specimens of the vegetative growth and flowers of my new carnation in different stages of development and is depicted in color as nearly true as it is reasonably possible to make the same in a color illustration of this character.

The following is a detailed description of my new carnation cultivar, Felicia with color terminology in accordance with Robert Ridgway's Color Standards and Nomenclature (1912 edition), except where general color terms of ordinary dictionary significance are acceptably definitive.

PLANT

Botanical classification: *Dianthus caryophyllus*.

Breeding:

*Female parent.*—My designation #1688 an unnamed seedling (not patented).

*Male parent.*—My designation #1981 an unnamed seedling (not patented).

Form: Erect but free-brancing.

Growth: Strong, heavy terminal with large side buds on weak secondary stems.

Classification: Greenhouse type, suitable for cut flower production as standard (one bloom per stem).

Propagation: Holds it distinguishing characteristics through succeeding propagations by rooted cuttings.

Locality where grown and observed: Encinitas, Calif.

Disease resistance: The new cultivar has shown no evidence of Fusarium or other rots, as determined by extensive tests in highly infested soils inoculated with as many strains of fungi as are locally available in the area of Encinitas, Calif.; tests were conducted without chemical or steam sterilization of the soil, and in soils in which the carnation plant "Sim" and others soon die.

Temperature tolerance: Not hardy to cold, but grows best at temperature above 10° C.; has good resistance to hot weather in summer months of August and September at Encinitas, Calif., without hardening of growth and with only little reduction of flower size and little flower fading; no marked fading of outer flower petals even when bloom is past maturity.

Blooming period: Blooms under both long and short photoperiods.

Height: First crop 60 cm., other crops approximately 1 meter.

Bud

Lobes of calyx overlap in tight bud and seldom split.

Length: 3 cm.

Diameter: 3 cm.

Color: Dull magenta purple; plate XXVI, 67 V-R-i. When petals unfurl, aster purple, plate XXII, 67 V-R-i.

PEDUNCLE

Strength: Strong.
Color: Dark green; plate XVII, 35° green m.

BLOOM

Size: Diameter to 7.5 cm., depth 3.5 cm.
Stem: Consists of 9 nodes. Length is from about 50 cm. Diameter is from about 5 mm., at base and about 3 mm. at base of calyx.
*Color.*—Dark green; plate XVII, 35′ Green.
Form: Dense, high crowned bloom.
Petalage: From 90–100 petals. Outer petals are about 3.5 cm. wide and about 5.0 cm. long. Center petals are about 2.0 cm. wide and about 4.0 cm. long.
*Color.*—The center of flower, outer petals, base of petals, inside of petals and reverse of petals are all aster purple, plate XII 67 V-R-i.
*General tonality.*—Uniform aster purple with few marginal white lines.
Petals: Texture is firm.
*Form.*—Outer petals semi-circular with irregular serrations 8 to 1 cm.
*Opening.*—Normal with minimum of split calyxes.
Fragrance: No distinctive fragrance.

FOLIAGE

Form: From flat to concave.
Size: About 1 cm. wide and 16–18 cm. long.
Quantity: Two leaves per node, with nodes spaced about 8 cm. apart.
Color: The upper and under sides of both young and mature plants are all dark green; plate XVII, 35′ green M.
Texture: Smooth.

I claim:

1. A new and distinct cultivar of carnation plant designated Felicia substantially as herein shown and described, characterized particularly as to novelty by the unique combination of a very vigorous and free-breaking plant habit, and strong and straight stems; superior resistance to the soil-borne diseases such as *Fusarium oxysporum* and *F. roseum* and rots such as damping off, water molds, and the like; large serrated flowers which open fully without bursting the calyx and causing "splits"; a distinctive and attractive magenta flower color which eventually fades evenly and beautifully; and good heat tolerance which is superior to that of the parent lines and the variety known as "Sim".

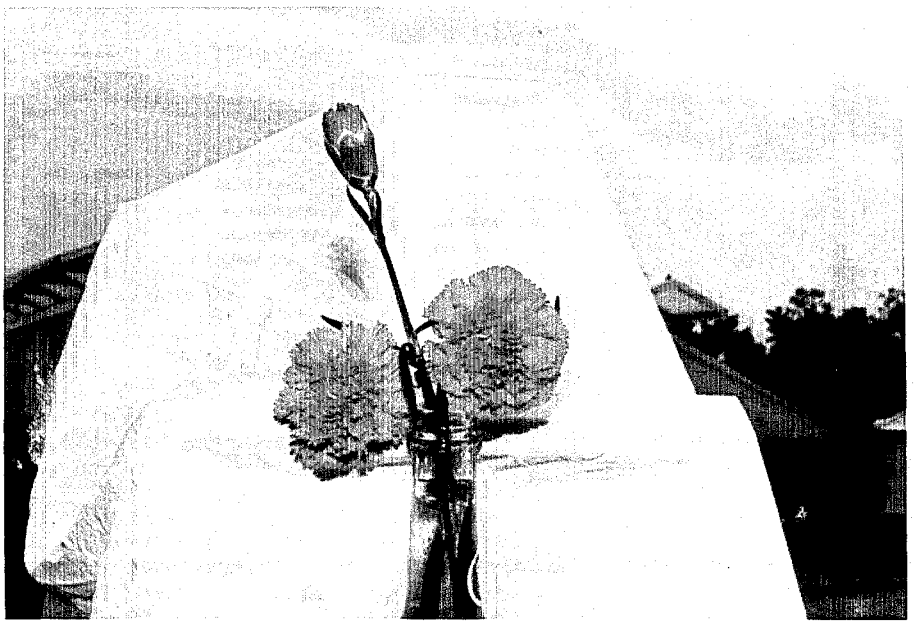

* * * * *